United States Patent
Tsuruta et al.

(10) Patent No.: US 9,826,888 B2
(45) Date of Patent: Nov. 28, 2017

(54) ENDOSCOPE HAVING POWER TRANSMISSION ELECTRODE AND TREATMENT TOOL HAVING POWER RECEPTION ELECTRODE, AND ENDOSCOPE SYSTEM

(71) Applicant: OLYMPUS CORPORATION, Tokyo (JP)

(72) Inventors: Shoei Tsuruta, Tachikawa (JP); Yuta Sugiyama, Hachioji (JP); Akira Matsui, Hino (JP)

(73) Assignee: OLYMPUS CORPORATION, Tokyo (JP)

( * ) Notice: Subject to any disclaimer, the term of this patent is extended or adjusted under 35 U.S.C. 154(b) by 240 days.

(21) Appl. No.: 14/842,288

(22) Filed: Sep. 1, 2015

(65) Prior Publication Data
US 2015/0366441 A1    Dec. 24, 2015

Related U.S. Application Data

(63) Continuation of application No. PCT/JP2014/050805, filed on Jan. 17, 2014.

(30) Foreign Application Priority Data

Jun. 28, 2013    (JP) ................. 2013-136761

(51) Int. Cl.
*A61B 1/018*    (2006.01)
*A61B 1/00*    (2006.01)
(Continued)

(52) U.S. Cl.
CPC .......... *A61B 1/018* (2013.01); *A61B 1/00029* (2013.01); *A61B 1/00087* (2013.01);
(Continued)

(58) Field of Classification Search
CPC ..... A61B 1/018; A61B 1/005; A61B 1/00071; A61B 1/00029; A61B 1/00027;
(Continued)

(56) References Cited

U.S. PATENT DOCUMENTS 3,569,777 A * 3/1971 Beaudry ................. H05H 1/30
                                                    156/345.44
5,249,585 A * 10/1993 Turner .................... A61B 5/01
                                                    600/549

(Continued)

FOREIGN PATENT DOCUMENTS

EP    0 888 749 A1    1/1999
JP    S60-083633 A2   5/1985
(Continued)

OTHER PUBLICATIONS

Extended Supplementary European Search Report dated Feb. 6, 2017 in European Patent Application No. 14 81 7175.4.
(Continued)

*Primary Examiner* — John P Leubecker
(74) *Attorney, Agent, or Firm* — Scully, Scott, Murphy & Presser, P.C.

(57) ABSTRACT

An endoscope system having: an endoscope having: an endoscope insertion section configured to be inserted into a subject, wherein the endoscope insertion section defines a channel having a distal opening; and a power transmission electrode arranged to the endoscope insertion section and electrically connected to a power source configured to output a high-frequency power; and a treatment tool having: an electrically powered treatment device; a treatment tool insertion section attached to the electrically powered treatment device, wherein the treatment tool insertion section is configured to be arranged in the channel of the endoscope; and a power reception electrode arranged to the treatment tool insertion section, wherein the power reception electrode
(Continued)

is separated from the power transmission electrode to form a capacitor to transfer power from the power source through an electric field between the power transmission electrode and the power reception electrode to power the electrically powered treatment device.

12 Claims, 10 Drawing Sheets

(51) Int. Cl.
    *H02J 50/05* (2016.01)
    *A61B 18/16* (2006.01)
    *A61B 18/00* (2006.01)
    *A61B 18/14* (2006.01)
    *A61B 17/00* (2006.01)
    *A61B 18/12* (2006.01)

(52) U.S. Cl.
    CPC ...... *A61B 18/1442* (2013.01); *A61B 18/1492* (2013.01); *H02J 50/05* (2016.02); *A61B 1/00124* (2013.01); *A61B 18/16* (2013.01); *A61B 2017/0034* (2013.01); *A61B 2017/00296* (2013.01); *A61B 2018/00178* (2013.01); *A61B 2018/00982* (2013.01); *A61B 2018/1286* (2013.01); *A61B 2018/1412* (2013.01); *A61B 2560/0214* (2013.01)

(58) Field of Classification Search
    CPC .... A61B 2560/0204; A61B 2560/0217; A61B 2018/00077; A61B 2018/00178; A61B 2018/00982; A61B 2560/0214; H02J 50/05
    See application file for complete search history.

(56) References Cited

U.S. PATENT DOCUMENTS

| | | | | |
|---|---|---|---|---|
| 5,585,766 | A | * | 12/1996 | Shel ............... H01J 37/32183 333/17.3 |
| 5,817,092 | A | * | 10/1998 | Behl ................. A61B 18/1206 606/1 |
| 5,849,020 | A | | 12/1998 | Long et al. |
| 5,916,215 | A | * | 6/1999 | Long ................. A61B 18/1487 606/41 |
| 6,022,362 | A | | 2/2000 | Lee et al. |
| 6,187,002 | B1 | | 2/2001 | Long et al. |
| 6,206,875 | B1 | | 3/2001 | Long et al. |
| 7,824,407 | B2 | | 11/2010 | Yamamoto et al. |
| 9,184,595 | B2 | * | 11/2015 | Kurs ....................... H02J 5/005 |
| 2004/0133189 | A1 | | 7/2004 | Sakurai |
| 2008/0015409 | A1 | * | 1/2008 | Barlow ............... A61B 18/1492 600/106 |
| 2010/0179384 | A1 | * | 7/2010 | Hoeg ................. A61B 1/00016 600/109 |
| 2011/0018359 | A1 | * | 1/2011 | Wada ..................... B60L 11/182 307/104 |
| 2011/0025132 | A1 | * | 2/2011 | Sato ........................ H02J 5/005 307/104 |
| 2011/0218402 | A1 | * | 9/2011 | Sato ................... A61B 1/00016 600/160 |
| 2011/0251606 | A1 | * | 10/2011 | Kerr ................... A61B 18/1402 606/34 |
| 2012/0184951 | A1 | * | 7/2012 | Viola ............... A61B 17/00234 606/34 |
| 2012/0209061 | A1 | | 8/2012 | Kato |
| 2012/0221002 | A1 | | 8/2012 | Long et al. |
| 2015/0057653 | A1 | * | 2/2015 | Sugiyama .......... A61B 17/3421 606/34 |

FOREIGN PATENT DOCUMENTS

| | | |
|---|---|---|
| JP | H03-054605 U1 | 5/1991 |
| JP | H03-280946 A | 12/1991 |
| JP | H08-052153 A2 | 2/1996 |
| JP | H11-099158 A2 | 4/1999 |
| JP | H11-128242 A2 | 5/1999 |
| JP | 2000-116657 A2 | 4/2000 |
| JP | 2000-254134 A2 | 9/2000 |
| JP | 2004-208922 A2 | 7/2004 |
| JP | 2007-117405 A2 | 5/2007 |
| JP | 2009-100873 A | 5/2009 |
| JP | 2010-252446 A | 11/2010 |
| JP | 2011-030317 A2 | 2/2011 |
| JP | 2014-004237 A2 | 1/2014 |
| WO | 2013/024419 A2 | 2/2013 |
| WO | WO 2014/002830 A1 | 1/2014 |

OTHER PUBLICATIONS

International Search Report dated Aug. 6, 2013 issued in PCT/JP2013/066735, together with English language translation.
International Search Report dated Apr. 22, 2014 issued in PCT/JP2014/050805, together with English language translation.
Written Opinion of the International Searching Authority dated Aug. 6, 2013 received in related International Application No. PCT/JP2013/066735, together with English language translation.

* cited by examiner

ENDOSCOPE HAVING POWER TRANSMISSION ELECTRODE AND TREATMENT TOOL HAVING POWER RECEPTION ELECTRODE, AND ENDOSCOPE SYSTEM

CROSS REFERENCE TO RELATED APPLICATION

This application is a continuation of PCT International Application No. PCT/JP2014/050805, filed on Jan. 17, 2014, the entire content of which is incorporated by this reference, and claims priority to Japanese Patent Application No. JP2013-136761, filed on Jun. 28, 2013, the entire content of which is incorporated by this reference.

BACKGROUND

The present invention relates to an endoscope system for feeding power wirelessly to a device passing through a channel of a flexible endoscope.

BACKGROUND ART

U.S. Pat. No. 7,824,407 discloses high-frequency incision forceps for applying high-frequency current to a body tissue to do a treatment as a device passing through a channel of a flexible endoscope and inserted into a body.

A cable is connected to devices such as the high-frequency incision forceps to supply power necessary for operation. However, this cable may disturb operator's operations and hence reduce operability.

U.S. Pat. No. 6,187,002 and U.S. Pat. No. 6,206,875 disclose that power is wirelessly fed from a transmission electrode of a trocar to a reception electrode of a capacitive cordless electrosurgical instrument inserted in the trocar through capacitive coupling.

It is an object of embodiments of the present invention to provide an endoscope system including a highly operable device inserted into a channel of a flexible endoscope.

SUMMARY

An endoscope system comprising an endoscope and a treatment tool is provided. The endoscope comprises: an endoscope insertion section configured to be inserted into a subject, wherein the endoscope insertion section defines a channel having a distal opening; and a power transmission electrode arranged to the endoscope insertion section, wherein the power transmission electrode is electrically connected to a power source configured to output a high-frequency power. The treatment tool comprises: an electrically powered treatment device; a treatment tool insertion section attached to the electrically powered treatment device, wherein the treatment tool insertion section is configured to be arranged in the channel of the endoscope; and a power reception electrode arranged to the treatment tool insertion section, wherein the power reception electrode is separated from the power transmission electrode to form a first capacitor to transfer power from the power source through an electric field between the power transmission electrode and the power reception electrode to power the electrically powered treatment device.

DETAILED DESCRIPTION

First Embodiment

Figure 1:
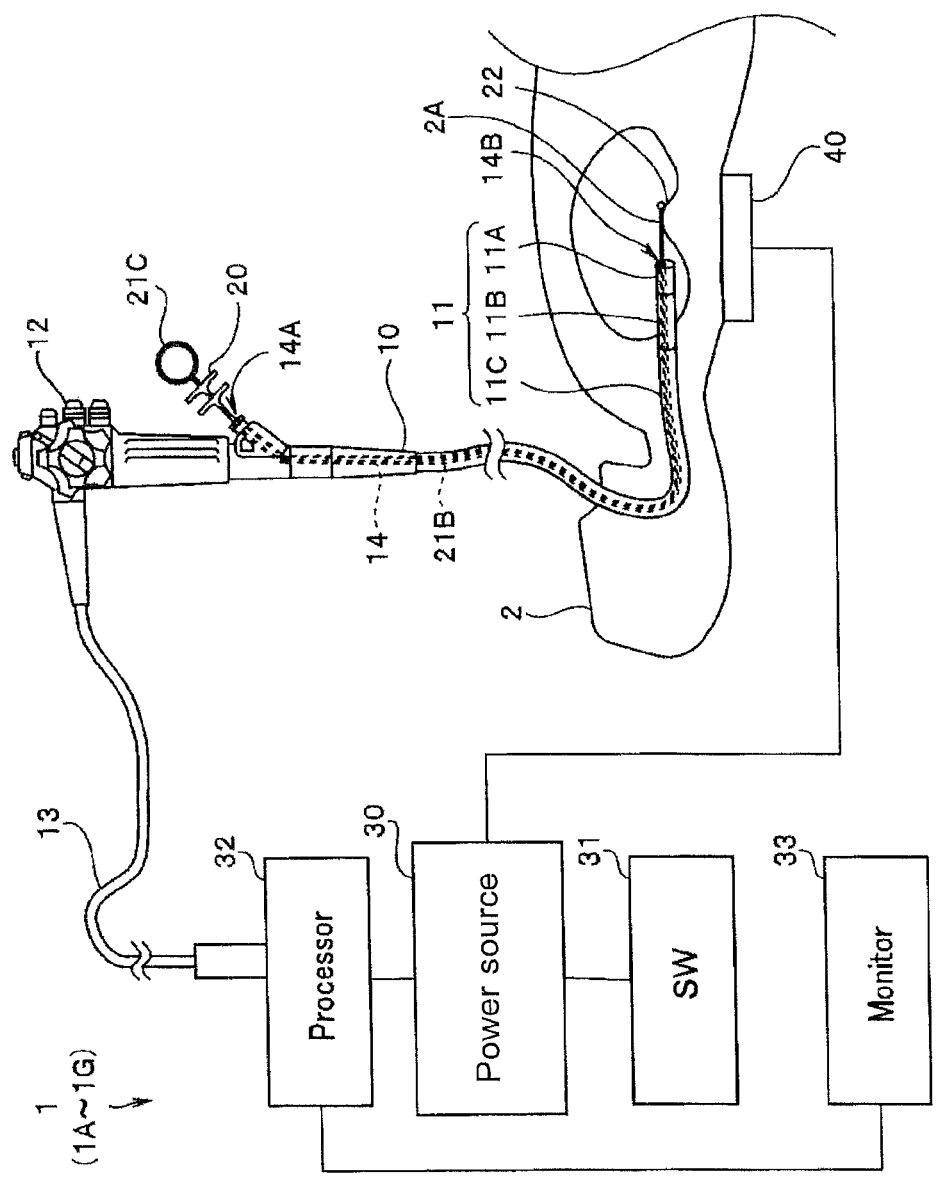
FIG. 1 is a configuration diagram of an endoscope system of a first embodiment.

As illustrated in FIG. 1, an endoscope system 1 of the embodiment comprises a flexible endoscope (hereinafter called "endoscope") 10, a treatment tool 20 as a device passing through a channel 14 of the endoscope 10, a power source 30, and a return electrode 40.

The endoscope 10 has an endoscope insertion section 11 and an operation section 12 arranged on a base end side of the endoscope insertion section 11, and a universal cord 13 provided to extend from the operation section 12. The endoscope insertion section 11 comprises a distal end portion 11A in which an imaging unit 15 (imaging sensor such as a CCD or a CMOS) (see FIG. 2) is arranged, a curved portion 11B for changing the direction of the distal end portion 11A, and a soft portion 11C being flexible and elongated. The operation section 12 is a non-flexible section grasped by an operator to perform a directional operation of the distal end portion 11A, an air supply operation, a water supply operation, an endoscopic image taking operation, and the like. On the other hand, the endoscope insertion section 11 is a flexible section to be inserted from the oral cavity or the anus of a patient as a subject 2 to be movably treated into an alimentary tract.

A processor 32 as a hardware connected to the universal cord 13 of the endoscope 10 comprises a control unit (not illustrated) composed of a CPU and the like for controlling the entire endoscope system 1 to process an imaging signal output from the imaging unit 15 and display an endoscopic image on a monitor 33. The power source 30 connected to the processor 32 supplies high-frequency power to the treatment tool 20. For example, a foot switch SW 31 controls ON/OFF of the output of the power supply 30. Note that a line branched from the universal cord 13 may be connected directly to the power source 30.

For example, the return electrode 40 made of a metal conductor such as stainless steel is a human body-side electrode. The return electrode 40 is applied to a subject (patient) 2 to be treated, for example, to come into contact with a wide area of the back side so as to form a so-called return circuit.

The endoscope 10 comprises a flexible channel 14 made of a resin tube passing through the endoscope insertion section 11 from an insertion opening 14A of the operation section 12 to a distal opening 14B of the distal end portion 11A.

Figure 3:
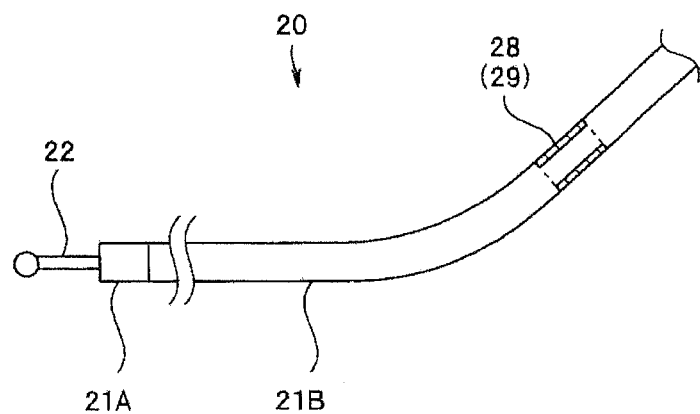
FIG. 3 is a schematic sectional view of a treatment tool in the endoscope system of the first embodiment.

As illustrated in FIG. 3, the treatment tool 20 can be a monopolar high-frequency electrosurgical knife comprising a distal end portion 21A in which a treatment unit (knife electrode) 22 is arranged, an treatment tool insertion section 21B can be flexible and elongated, and an operation section 21C arranged on the base end side of the treatment tool insertion section 21B and operated by the operator outside the body. The treatment tool 20 is inserted from the insertion opening 14A to pass through the channel 14 and project the distal end portion 21A from the distal opening 14B.

The power source 30 outputs high-frequency power, for example, with a frequency of not less than 100 kHz and not more than 100 MHz. The frequency of the high-frequency power is preferably selected from frequencies allowed by the laws and the like, which is 13.56 MHz, for example. It is preferred, but not particularly limited to, that the waveform amplitude of the high-frequency power be of a sinusoidal wave because a general-purpose power supply can be used.

In the endoscope system 1, the treatment tool 20 and the power source 30 are not connected by wire. However, when the treatment tool 20 is inserted into the channel 14, the treatment tool 20 receives, in wireless power transmission, power required to do a treatment from the power source 30 through the endoscope 10. Note that the wireless power transmission is the same in meaning as wireless power supply.

Figure 2:
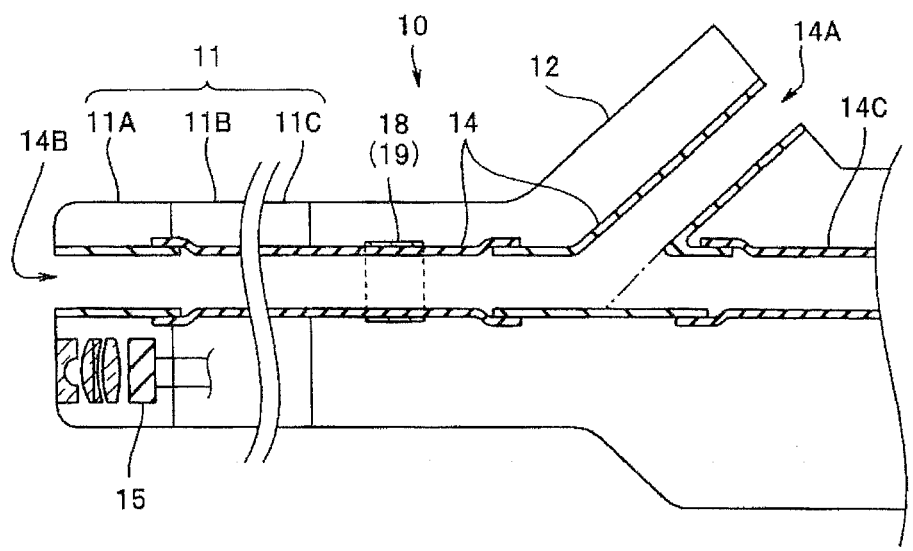
FIG. 2 is a schematic sectional view of an endoscope in the endoscope system of the first embodiment.
Figure 4:
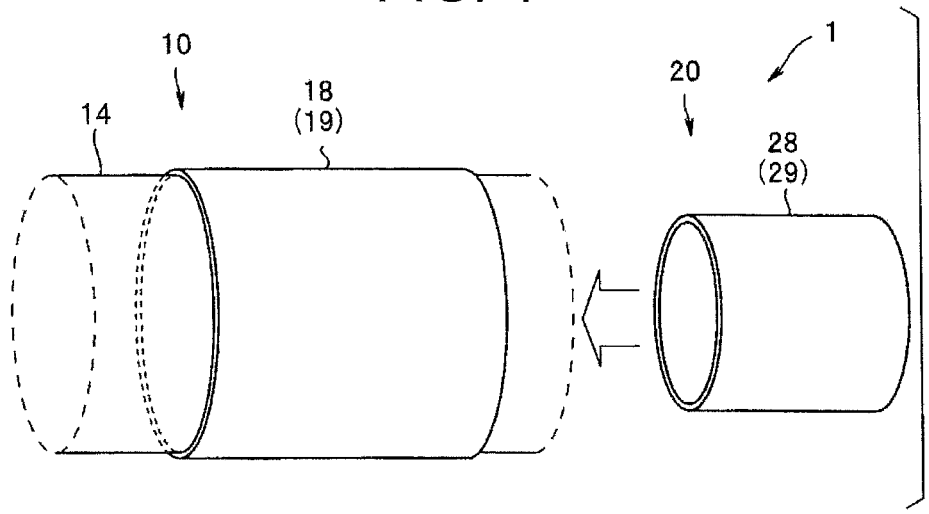
FIG. 4 is a schematic diagram of a transmission electrode and a reception electrode in the endoscope system of the first embodiment.

In other words, as illustrated in FIG. 2 and FIG. 4, the endoscope 10 comprises a power transmission unit 19 comprising a power transmission electrode 18 to convert the high-frequency power output from the power source 30 into an alternating electric field. The power transmission electrode 18 of the endoscope 10 is made of a cylindrical conductor laid to cover the outer circumference of the channel 14. The channel 14 comprises a flexible tube and a branch tube, and one side of the branch tube is connected to an air sending and sucking tube 14C.

The power transmission unit 19 may be structured to have a hollow section with which part of the channel 14 is replaced as long as it is located inside of at least either of the operation section 12 and the endoscope insertion section 11. In other words, in this specification, a component that forms the hollow section in the above structure is also regarded as part of the channel 14.

Although the conductor of the power transmission electrode 18 may be exposed to the inner surface of the hollow section in terms of the function as an electrode, it is preferred that the inner surface of the hollow section be sealed by an insulating material because the channel 14 is also used for sending and sucking air, and the like.

On the other hand, as illustrated in FIG. 3 and FIG. 4, the treatment tool 20 comprises a power reception unit 29 comprising a power reception electrode 28 to receive an alternating electric field. The power reception electrode 28 of the treatment tool 20 is made up of a cylindrical conductor laid along the outer circumferential surface of the treatment tool insertion section 21B.

Note that a region of part of the treatment tool insertion section 21B, where the power reception electrode 28 is arranged, is so arranged that the conductor will not be exposed to the outermost circumferential surface, and if it can be inserted into the channel 14, the outer diameter $\phi$ (20) of the region may be made larger than other regions.

Figure 5A:
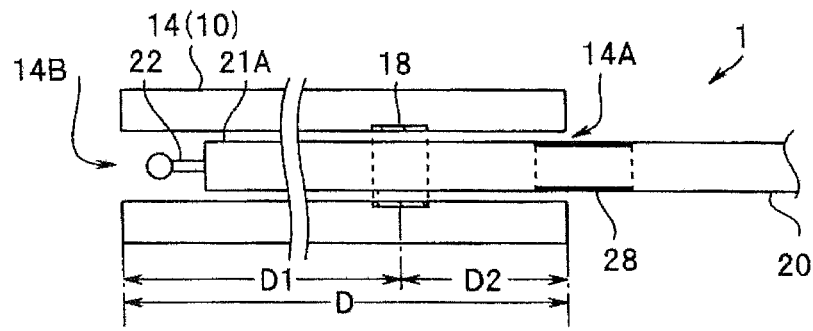
FIG. 5A is a sectional view of the transmission electrode and the reception electrode in the endoscope system of the first embodiment.

Here, as illustrated in FIG. 5A, even when the treatment tool 20 is inserted into the channel 14 from the insertion opening 14A, the power reception electrode 28 of the treatment tool 20 cannot efficiently receive an alternating electric field generated by the transmission electrode 18 of the endoscope 10 until the treatment unit 22 protrudes from the distal opening 14B.

Figure 5B:
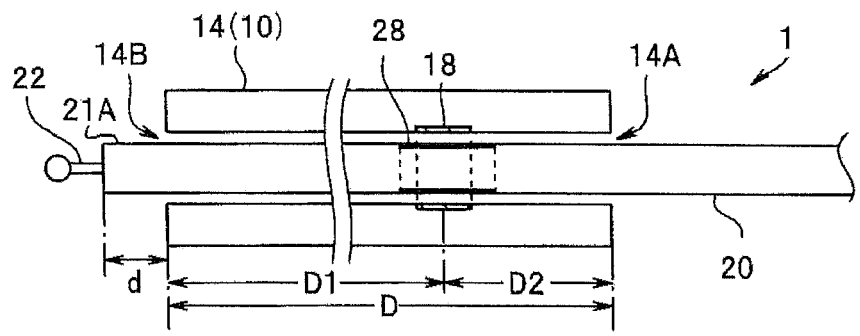
FIG. 5B is a sectional view of the transmission electrode and the reception electrode in the endoscope system of the first embodiment.

On the other hand, in a state where the treatment unit 22 is protruding from the distal opening 14B as illustrated in FIG. 5B, the power reception electrode 28 is in a state of being inserted in the transmission electrode 18. Therefore, in the endoscope system 1, the power reception electrode 28 and the transmission electrode 18 are strongly capacitively coupled to each other in the state where the treatment unit 22 is protruding from the distal opening 14B so that the alternating electric field generated by the power transmission electrode 18 can be received efficiently.

The power transmission electrode 18 laid along the outer surface of the cylindrical channel, and the power reception electrode 28 laid along the outer surface of the cylindrical treatment tool are both cylindrical.

Figure 6:
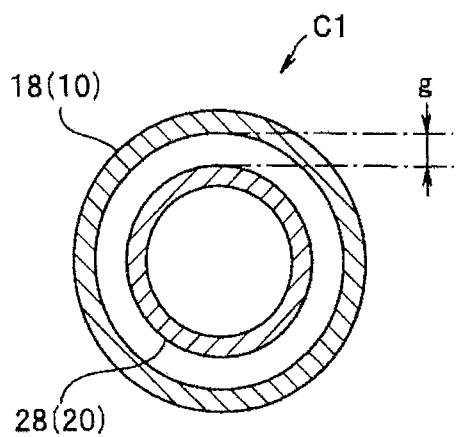
FIG. 6 is a sectional view of the transmission electrode and the reception electrode in the endoscope system of the first embodiment.

Therefore, in a state where the power reception electrode 28 is inserted in the transmission electrode 18 as illustrated in FIG. 6, the transmission electrode 18 and the power reception electrode 28 arranged opposite to each other in a concentric fashion form a first capacitor C1.

In the endoscope system 1, the treatment tool 20 has no physical contact (connection) with the endoscope 10 through the conductor. However, the power reception unit 29 of the treatment tool 20 is capacitively coupled to the power transmission unit 19 of the endoscope 10.

Figure 7:
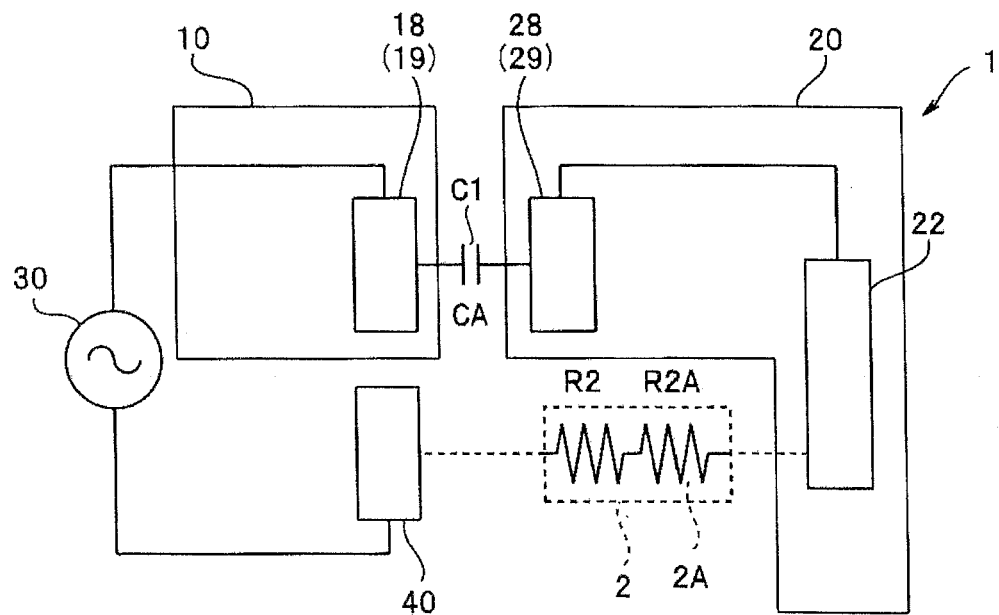
FIG. 7 is an equivalent circuit diagram of the endoscope system of the first embodiment.

FIG. 7 is a circuit diagram of the endoscope system 1. The high-frequency power output from the power source 30 is output to the treatment unit 22 through the capacitor C1 formed by the power transmission unit 19 of the endoscope 10 and the power reception unit 29 of the treatment tool 20.

When the treatment unit 22 comes in contact with a body tissue (affected area) as a treated area 2A, the high-frequency power is supplied between the treatment unit 22 and the return electrode 40.

Note that wiring for connection between the power source 30 and the return electrode 40 may be at a ground potential.

The power of the return circuit flowing from the subject 2 to be treated to the return electrode 40 flows through a large-area path. In other words, resistance R2 of the subject 2 to be treated is low. On the other hand, since the power is applied locally in the treated area 2A, resistance R2A of the treated area 2A is high and the density is high. Therefore, the applied power has little influence on the subject 2 to be treated, while the Joule heat is generated in the treated area 2A being in contact with the treatment unit 22 so that the treated area 2A will be subjected to a treatment (exsection/hemostasis).

Here, the efficiency of wireless transmission through capacitive coupling is proportional to the magnitude of capacitive coupling between the power transmission electrode 18 and the power reception electrode 28, i.e. capacitance CA of the capacitor C1 formed by the power transmission electrode 18 and the power reception electrode 28.

The capacitance C of the capacitor is proportional to a dielectric constant $\in$ between electrodes and a counter electrode area A, and inversely proportional to an inter-electrode distance g.

In other words, $C = \in A/g$.

As illustrated in FIG. 6, the inner diameter $\phi$ (14) of the channel 14 is larger than the outer diameter $\phi$ (20) of the treatment tool insertion section 21B so that the treatment tool insertion section 21B of the treatment tool 20 can be inserted. For example, $\phi$ (14)=2.8 mm and $\phi$ (20)=2.6 mm. Assuming that the thickness of the channel 14 is regarded as zero, when the electrodes of the capacitors C1 are coaxial with each other and not eccentric, the inter-electrode distance g therebetween is very short as 0.1 mm. Further, the counter electrode area A is proportional to a length L of a shorter electrode.

Therefore, it is preferred that the length of the power transmission electrode 18 and the power reception electrode 28 be 1 cm or more. If the length is in the above range or more, power can be transmitted and received. On the other hand, the maximum length of the power transmission electrode 18 and the power reception electrode 28 is determined by a length D of the channel 14. For example, the channel length D of the flexible endoscope 10 is about not less than 100 cm and not more than 230 cm, such as 200 cm. Thus, the maximum length of the power transmission electrode 18 is about D, and the maximum length of the power reception electrode 28 is also about D. Note that it is particularly preferred that the length of the power transmission electrode 18 and the power reception electrode 28 be not less than 5 cm and not more than 200 cm in terms of the transmission/reception efficiency and the self-inductance.

Note that an insulating material comprising a high dielectric constant $\in$, such as fluorocarbon resin, may be arranged between the power transmission electrode 18 and the power reception electrode 28 to increase the capacitance C.

The capacitance C may be increased by a mechanism for making the center positions of the power transmission electrode 18 and the power reception electrode 28 eccentric to each other, or a mechanism for pressing the channel with the power transmission electrode 18 laid to deform to the center side or to one side in order to reduce the inter-electrode distance g locally.

A state in which the capacitance becomes the highest with the electrodes made not eccentric is a state in which the power reception electrode 28 is inserted into the entire length of the power transmission electrode 18. Therefore, it is preferred that the length of the power reception electrode 28 be longer than the length of the power transmission electrode 18, and in light of the protrusion amount d from the distal opening 14B of the treatment tool 20, it is particularly preferred that the total length of the power reception electrodes 28 be (length of the power transmission electrode 18+protrusion amount d). Note that the protrusion amount d is, for example, not less than 1 cm and not more than 10 cm, though it depends on the treatment tool.

The minimum length of these electrodes is a length at which parasitic capacitance in the circuit and capacitance involved in transmitting/receiving power, i.e. the capacitance CA of the capacitor C1 becomes substantially the same as each other. When the parasitic capacitance in the circuit is higher than the capacitance involved in transmitting/receiving power, most of the supplied power does not reach the treatment unit.

Further, when the treatment unit consumes more of the power input from the power transmission unit to the power reception unit, transmission efficiency becomes higher. Therefore, it is preferred that the load on the treatment unit, i.e., the resistance should be large compared with various resistive components in the circuit.

In other words, although the example in which the power transmission electrode 18 is arranged in the operation section 12 of the channel 14 is illustrated in FIG. 2, it may be arranged in the soft portion 11C of the channel 14, or arranged in the operation section 12 and the soft portion 11C of the channel 14. Further, the first transmission electrode 18A may be arranged in the operation section 12 of the channel 14 and the second transmission electrode 18B may be arranged in the soft portion 11C of the channel 14.

Further, although the length of the power reception electrode 28 illustrated in FIG. 3 is short, it may be, for example, an electrode comprising almost the same length as the length of the treatment tool insertion section 21B.

The power transmission electrode 18 and the power reception electrode 28 are only need to be arranged in positions where the electrodes are strongly capacitively coupled to each other when the treatment unit 22 is in operation. Note that the power transmission electrode 18 and the power reception electrode 28 placed inside the flexible, soft portion 11C need to be flexible.

In the endoscope system 1, the channel 14 is so used that a capacitor C1 short in inter-electrode distance g, wide in counter electrode area A, and high in capacitance CA can be formed.

Although the length D of the channel 14 of the endoscope 10 is very long as 100 cm or more, most of the length is placed inside the flexible, soft portion 11C. The endoscope system 1 including the flexible endoscope 10 comprising the endoscope insertion section 11 (channel 14) is high in the efficiency of wireless power transmission because it can increase the length of the power transmission electrode 18 and the power reception electrode 28 according to the length of the endoscope insertion section 11.

Further, since the capacitor C1 is made up of concentric counter electrodes, even when the treatment tool 20 rotates in the channel 14 around the longitudinal direction as its axis, the power transmission electrode 18 and the power reception electrode 28 are capacitively coupled stably. Thus, the operator can carry out an insertion operation without being conscious of the rotation of the treatment tool 20.

As already described, the power transmission electrode 18 is made of cylindrical metal laid to cover the outer circumference of the channel 14. For example, a metal film made of copper or the like is formed on the outer circumferential surface of the channel 14 as a flexible tube by an evaporation method or a plating method to enable the formation of the power transmission electrode 18.

The power reception electrode 28 can also be made by forming a metal film on the outer circumferential surface of the treatment tool insertion section 21B of the treatment tool 20 in the same manner as the power transmission electrode 18. Note that it is preferred that the surfaces of the power transmission electrode 18 and the power reception electrode 28 should be covered with insulating films to ensure the insulating performance and reliability.

The power transmission electrode 18 and the power reception electrode 28 made of the metal films are easy to be laid on curved surfaces, and have flexibility.

Here, it is preferred that the same treatment tool 20 can be used even for multiple endoscopes different in channel length D. To this end, it is preferred that the arrangement position of the power transmission electrode 18 should be set with reference to the distal opening 14B. In other words, the power transmission electrode 18 of the endoscope only needs to be arranged in a position a predetermined distance D1 from the distal opening 14B. In this case, distance D2 from the insertion opening 14A to the power transmission electrode 18 in an endoscope comprising a longer channel length D becomes longer than that of an endoscope comprising a shorter channel length D.

In an endoscope system including multiple endoscopes, in each of which the power transmission electrode 18 is arranged in a position a predetermined distance D1 from the distal opening 14B, respectively, and the treatment tool 20, the multiple endoscopes can wirelessly feed power to the treatment tool 20 efficiently.

It goes without saying that an endoscope system including one endoscope and multiple treatment tools has the same effect, where the power reception unit 29 is arranged in a position capable of receiving the alternating electric field generated by the power transmission unit 19 most efficiently in a state of inserting each of the treatment tools into the channel 14 up to the operating position, respectively.

In an endoscope system 1, as illustrated in an equivalent circuit diagram of FIG. 7, an endoscope side circuit including a power source 30 and a power transmission unit 19 has no physical contact through a conductor with a treatment tool side circuit including a power reception unit 29 and a treatment unit 22 to apply current to a body tissue LT as a load section that consumes power.

However, the power reception unit 29 is capacitively coupled to a non-radiative alternating electric field generated in a space near the power transmission unit 19. The power is supplied to the treatment unit 22 of the treatment tool 20 through the power reception unit 29 capacitively coupled.

Since the treatment tool 20 in the endoscope system 1 has no wiring (cable) connected to the power source 30, it is easy to handle the treatment tool 20 with good operability. Further, since the power transmission unit 19 is arranged inside the endoscope 10, a generated electromagnetic field is less likely to leak outside the endoscope 10, and the influence of the leakage electromagnetic field on peripheral devices is small. Further, since distance between a living body as a subject to be treated and the power transmitting/receiving units is ensured, the influence of heat generation is small.

Further, since the cylindrical reception electrode 28 is coaxial with the cylindrical transmission electrode 18 and the counter electrode area is largest among same-sized counter electrodes, the capacitance C of the capacitor is high. In addition, since the power reception electrode 28 and the power transmission electrode 18 can be arranged over the entire length of the endoscope insertion section 11 of the flexible endoscope 10, it is easy to further increase the capacitance.

Further, since a relative positional relationship between the power transmission unit 19 and the power reception unit 29 is defined by arranging the power transmission unit 19 inside the endoscope 10, the state of strongly capacitive coupling between the power transmission unit 19 and the power reception unit 29, i.e., a state of high power transmission efficiency can be maintained stably, and energy saving performance is excellent as well.

Here, in the endoscope system 1, the switch 31 is used to control ON/OFF of the power output to the treatment tool 20 as already described above. The switch is illustrated as the foot switch 31 in FIG. 1, but the switch may be arranged in the power source 30, the operation section 12 of the endoscope 10, or the operation section 21C of the treatment tool 20.

The switch connected to the power source 30 or the switch arranged in the power source 30 controls ON/OFF of the output of the power source 30. The switch arranged in the operation section 12 or the operation section 21C controls ON/OFF of power through an internal circuit of the power transmission unit 19 or the power reception unit 29. Instead of the ON/OFF control in the power transmission/reception circuit, a Q value of the power transmission/reception circuit can be increased/decreased to make a vast change in transmission/reception efficiency in order to obtain the same effect as the ON/OFF control. However, when the amount of power is large, the control of decreasing the Q value may cause a problem such as heat generation.

Note that the switch may be a button switch, a touch gesture-capable operating part, a speech-recognition operating part, or the like.

As described above, in the endoscope system 1, the switch as power transmission starting/stopping means for starting or stopping output from the power source 30 is arranged separately from the power source 30, or arranged in the operation section 12 of the endoscope 10 or in the treatment tool 20.

Variations of First Embodiment

Next, endoscope systems 1A to 1G, and the like as variations 1 to 6 of the first embodiment will be described. Since the endoscope systems 1A to 1G, and the like comprises the same components as the endoscope system 1 already described and are similar to the endoscope system 1, the same reference numerals are given to components having the same functions to omit the description thereof.

All the endoscope systems 1A to 1G, and the like have the effects of the endoscope system 1, and further have more beneficial effects than the endoscope system 1, respectively.

<Variation 1> Resonance Circuit

Figure 8:
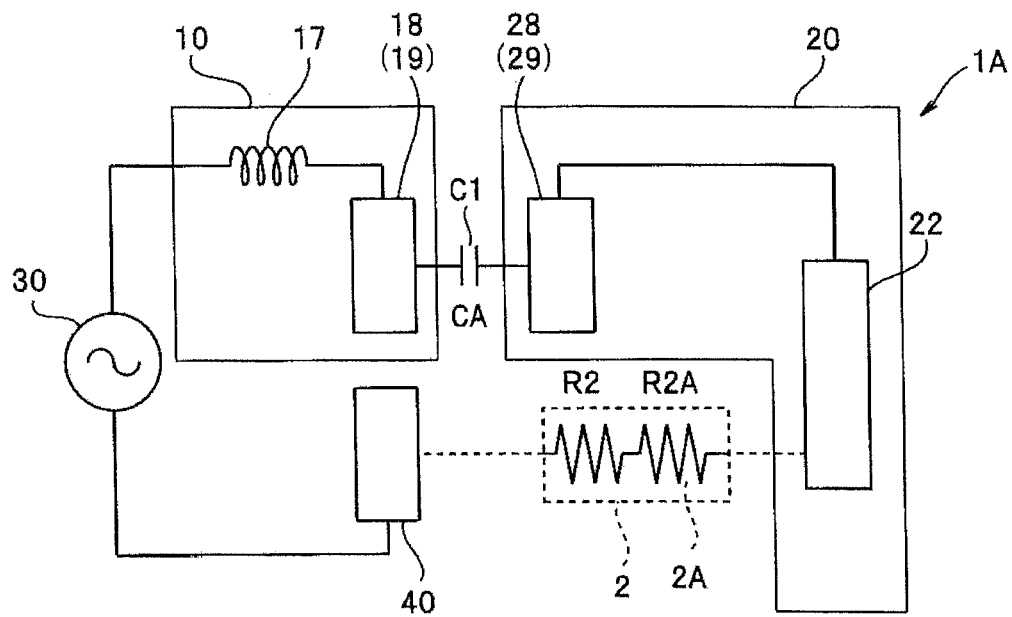
FIG. 8 is an equivalent circuit diagram of an endoscope system as a variation 1 of the first embodiment.

As illustrated in FIG. 8, the endoscope system 1A has an inductance element 17 in a power transmission/reception circuit including the power transmission unit 19 of the endoscope 10 and the power reception unit 29 of the treatment tool 20. The addition of an inductance component causes the power transmission/reception circuit to form a serial resonance circuit with a predetermined resonant frequency F1.

Then, circuit capacitance Ctotal including the capacitance CA of the capacitor C1, circuit inductance Ltotal including the inductance element 17, and a frequency F0 of high-frequency power output from the power source 30 have the following relation (Equation 1).

$$\sqrt{Ltotal \cdot Ctotal} = 1/2\pi F1 = 1/2\pi F0 \qquad \text{(Eq. 1)}$$

In other words, the frequency F0 of the high-frequency power output from the power source 30 coincides with the resonant frequency F1 of the power transmission/reception circuit. Therefore, the high-frequency power output from the power source 30 is efficiently output to the treatment unit 22.

Instead of the inductance element 17, the power reception unit 29 of the treatment tool 20 may comprises an inductance element, or the power transmission unit 19 and the power reception unit 29 may comprises inductance elements, respectively. Further, when the power transmission/reception circuit is a resonance circuit comprising the resonant frequency F1 as a whole, the inductance element may be arranged in the processor 32.

Here, voltage across the terminals of the inductance element in the resonance circuit is the same as the voltage across the terminals of the capacitor, and the inductance of the inductance element is set to compensate for a reactance using the capacitance of the capacitor and a specific frequency. Here, when only the voltage across the terminals of a more essential capacitor is discussed, the voltage across the terminals is inversely proportional to the capacitance. Therefore, the higher the capacitance of the capacitor, the lower the voltage across the terminals, and this can lead to reducing risk of insulation breakdown. However, when the capacitance is too high, self-resonance may occur due to the self-inductance of the resonance circuit even without any inductance element 17, and this can deteriorate controllability. The capacitance needs to be low to arrange an inductance element in order to improve controllability. Thus, the capacitance is set in consideration of trade-off between the risk of insulation breakdown and controllability. Since the voltage across the terminals of the inductance element is proportional to the inductance, though not described in detail, the inductance element acts in an opposite way to the capacitance element.

<Variation 2> Resonance Control

Figure 9:
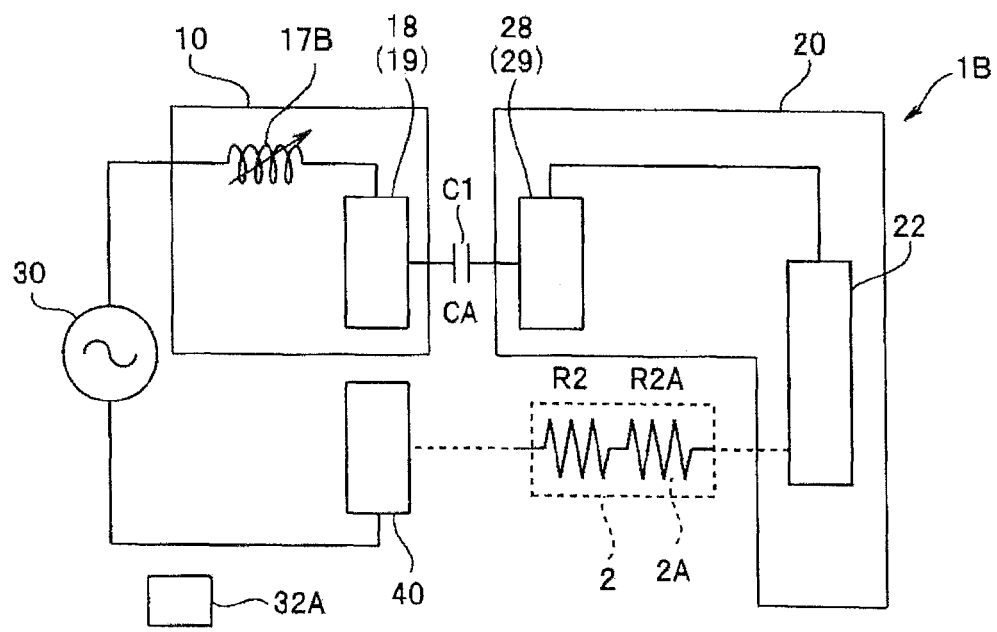
FIG. 9 is an equivalent circuit diagram of an endoscope system as a variation 2 of the first embodiment.

As illustrated in FIG. 9, an endoscope system 1B has a variable inductance element 17B. Then, a control unit 32A adjusts the inductance of the variable inductance element 17B to make the resonant frequency F1 of the resonance circuit coincide with the frequency F0 of high-frequency power output from the power source 30. The control unit 32A is, for example, arranged in the processor 32, the power source 30, or the endoscope 10.

When the positional relationship between the power transmission electrode 18 and the power reception electrode 28, the treatment condition, or the like is changed, the resonant frequency F1 of the resonance circuit varies because the capacitance of the capacitor C1 varies. However, in the endoscope system 1B, the resonant frequency F1 is adjusted to coincide with the frequency F0 of high-frequency power.

Therefore, power input from the power source 30 to the resonance circuit is highly efficient.

Note that the control unit 32A may control the power source 30 according to the change in the resonant frequency F1 of the power transmission/reception circuit to change the frequency F0 of high-frequency power or an output value of the high-frequency power.

In the above description, the inductance element 17, 17B is described as part of the power transmission unit 19, but the inductance element 17, 17B and the control unit 32A may be, for example, part of the processor 32. Further, the inductance element 17 and the like may be arranged in the operation section 21C of the treatment tool 20. In other words, the inductance element 17, 17B and the control unit 32A have only to be comprised in any of the components in the endoscope system 1A, 1B.

When a power supply with a nonzero output impedance, for example, a 50Ω power supply is used as the power source 30, an impedance matching circuit may be arranged before the power transmission unit to make the impedance on the treatment unit side of the power transmission unit coincide with the output impedance of the power source in order to suppress reflection so that the efficiency of power input from the power source 30 to the resonance circuit will be increased.

The impedance matching circuit composed of a combination of two or more elements such as a capacitance element and an inductance element may be part of the processor 32, or may be arranged in the operation section 21C of the treatment tool 20.

<Variation 3> Electrode Structure

The distribution of a generated alternating electric field, a capacitive coupling state, and the like greatly vary depending on the structure and arrangement of the power transmission electrode 18 and the power reception electrode 28. However, power can be wirelessly transmitted as long as the structure is such that an alternating electric field generated in the power transmission unit 19 causes capacitive coupling to the power reception unit 29.

In the endoscope system 1, although the description is made by taking the cylindrical metal films as an example of the power transmission electrode 18 of the power transmission unit 19 and the power reception electrode 28 of the power reception unit 29, the electrodes for generation of an alternating electric field and power reception are not limited to the cylindrical metal films. FIG. 10A to FIG. 13 illustrate electrodes as variations of the power transmission electrode 18 and the power reception electrode 28.

Note that the structure of the power reception electrode 28 of the power reception unit 29 may be the same as or different from the power transmission electrode 18 of the power transmission unit 19.

Figure 10A:
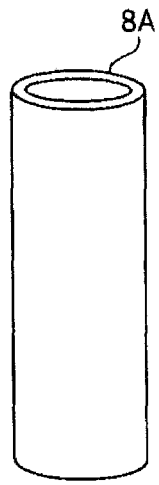
FIG. 10A is a schematic diagram of an electrode as a variation 3 of the endoscope system of the first embodiment.
Figure 10B:
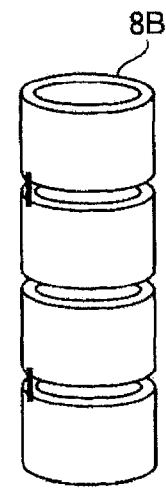
FIG. 10B is a schematic diagram of an electrode as the variation 3 of the endoscope system of the first embodiment.
Figure 10C:
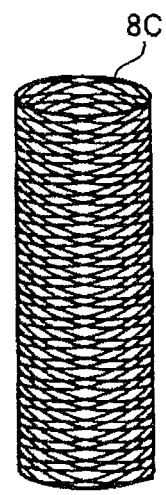
FIG. 10C is a schematic diagram of an electrode as the variation 3 of the endoscope system of the first embodiment.
Figure 10D:
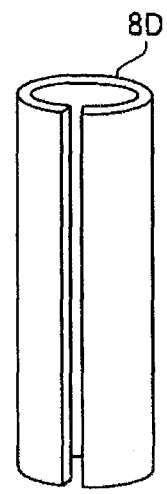
FIG. 10D is a schematic diagram of an electrode as the variation 3 of the endoscope system of the first embodiment.
Figure 10E:
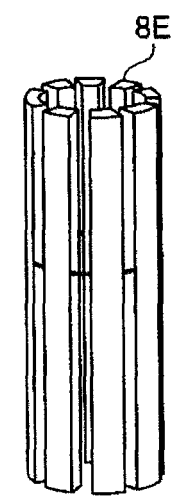
FIG. 10E is a schematic diagram of an electrode as the variation 3 of the endoscope system of the first embodiment.

An electrode 8A in FIG. 10A is made of a metal member, made by shaping copper foil or the like into a cylinder, or of a copper tube or the like. An electrode 8B in FIG. 10B is made by coupling multiple cylindrical metal members and electrically connecting the metal members. The electrode 8B will have flexibility even if each of the cylindrical metal members has low flexibility. Since an electrode 8C in FIG. 10C is made of a metal member formed into a mesh, it has flexibility. Since an electrode 8D in FIG. 10D has a slit formed in the longitudinal direction, a reduction in eddy current loss is small. Since an electrode 8E in FIG. 10E is divided into multiple elongated members, it has flexibility.

Figure 10F:
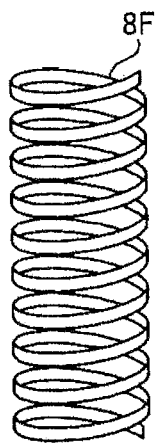
FIG. 10F is a schematic diagram of an electrode as the variation 3 of the endoscope system of the first embodiment.
Figure 10G:
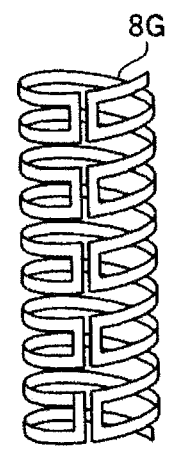
FIG. 10G is a schematic diagram of an electrode as the variation 3 of the endoscope system of the first embodiment.
Figure 10H:
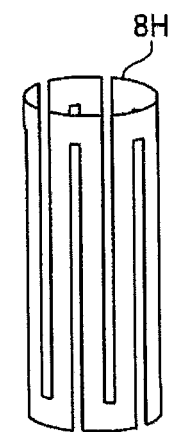
FIG. 10H is a schematic diagram of an electrode as the variation 3 of the endoscope system of the first embodiment.

An electrode 8F in FIG. 10F has a spiral form. Although adjacent element wires are in non-contact with each other in the electrode 8F, it is preferred that the electrode 8F be a so-called densely wound coil with adjacent element wires being in contact and conductive with each other to reduce self-inductance. An electrode 8G in FIG. 10G is formed into a spiral shape comprising folded portions. An electrode 8H in FIG. 10H has folded portions at the edges in the longitudinal direction.

Here, a so-called densely wound spiral coil with adjacent element wires being substantially in contact with each other may be arranged in the treatment tool insertion section 21B of the treatment tool 20 to ensure flexibility and mechanical strength. In this case, the power reception electrode 28 can be formed by using part of a shape holding spiral coil of the treatment tool 20, which has the same structure as the electrode 10F, to reduce the size and cost of the treatment tool 20.

In other words, a conducting wire for energization is connected to the shape holding spiral coil so that it can be used as the power reception electrode 28. When the shape holding spiral coil is made of stainless steel or the like having a relatively high electric resistance, it is preferred that a low-resistance metal material should be formed on the surface by plating with copper, silver, or the like to reduce the electric resistance. Alternatively, at least part of the stainless coil may be replaced by a coil made of a low-resistance metal material so that it will be used as the power reception electrode 28.

Figure 11:
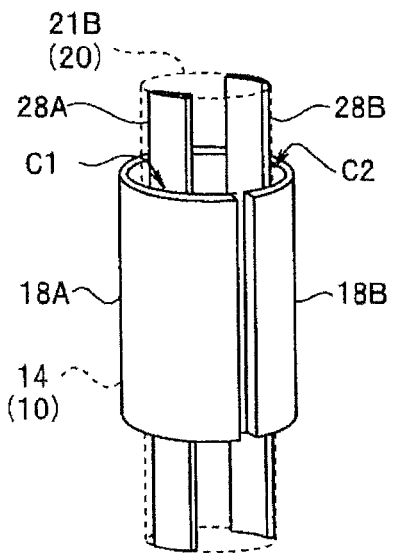
FIG. 11 is a schematic diagram of electrodes as the variation 3 of the endoscope system of the first embodiment.
Figure 12:
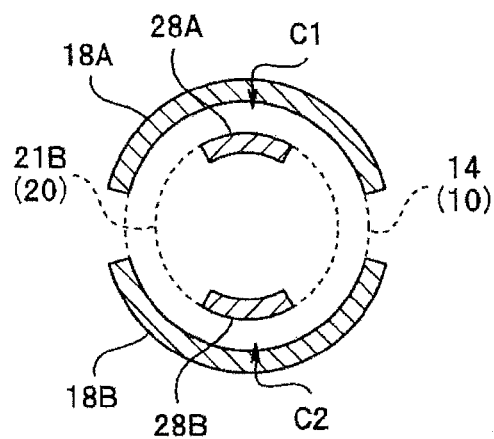
FIG. 12 is a sectional view of the electrodes as the variation 3 of the endoscope system of the first embodiment.

Further, as illustrated in FIG. 11 and FIG. 12, and the like, the electrodes may be transmission electrodes 18A and 18B, and power reception electrodes 28A and 28B, obtained by dividing each electrode into two in the circumferential direction.

Figure 13:
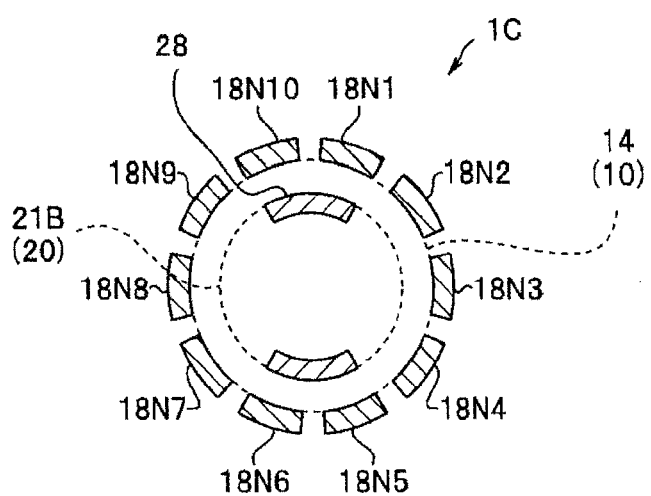
FIG. 13 is a sectional view of electrodes as the variation 3 of the endoscope system of the first embodiment.

In an endoscope system 1C illustrated in FIG. 13, the power transmission electrode 18 is divided into ten parts, i.e., power transmission electrodes 18N1 to 18N10. The power transmission electrodes 18N1 to 18N10 are connected to the power source 30 through respective switching elements (not illustrated). The treatment tool 20 is rotatable inside the channel 14.

In the endoscope system 1C, one of the power transmission electrodes 18N1 to 18N10 is selected as being capacitively coupled most strongly to the power reception electrode 28 to form the capacitor C1.

In the endoscope system 1C, a reduction in power transmission efficiency due to the generation of eddy current is suppressed.

It is preferred that the number of electrode divisions be not less than three and not more than 20. A predetermined effect can be obtained within the above range. Further, the power reception electrode 28 may be divided instead of the power transmission electrode 18, or the power transmission electrode 18 and the power reception electrode 28 may be divided.

<Variation 4> Shielding Member

Figure 14:
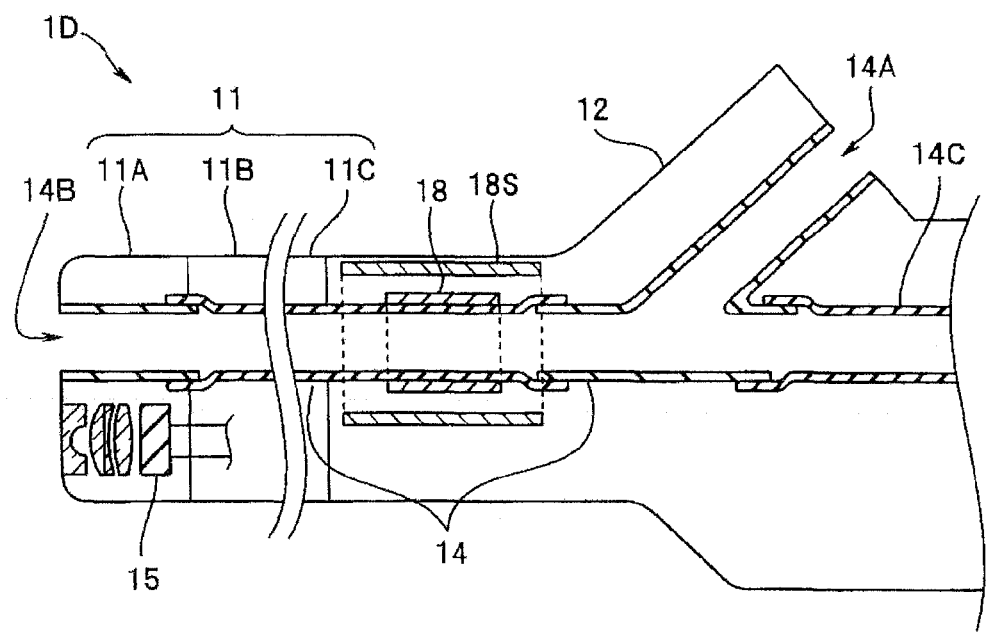
FIG. 14 is a sectional view of power transmission/reception units in an endoscope system as a variation 4 of the first embodiment.

In the endoscope system 1, since the power transmission unit 19 is arranged inside the endoscope 10 as already described, a generated electromagnetic field is less likely to leak outside the endoscope 10. In order to prevent a further leakage electromagnetic field, an endoscope system 1D comprising an endoscope 10D with a shielding member 18S arranged therein to shield an electromagnetic field as illustrated in FIG. 14 is preferable. Although the shielding member 18S only needs to be arranged to cover at least part of the outer circumference of the power transmission electrode 18, it is preferred that shielding member 18S should be arranged to cover the outer circumference completely.

As the shielding member 18S, a conductive material, for example, a metal material such as gold, silver, copper, aluminum, or stainless steel, highly doped semiconductor, conductive resin, or the like is used. The shielding member 18S may be connected to the ground (ground-connected).

As described above, the power transmission unit 19 is covered with the shielding member 18S in the endoscope system 1D.

<Variation 5> Treatment Tool

As devices in the endoscope system 1, various monopolar treatment tools, each comprising a load section operating with power received by the power reception unit 29, can be used. In other word, for example, high-frequency incision forceps, high-frequency hemostatic forceps, hot biopsy forceps, a high-frequency coagulation treatment tool, or the like can be used as the treatment tool 20.

In an endoscope system including multiple treatment tools different in required power, since the output of the power source 30 needs to be adjusted according to the load of each of the treatment tools, the operation is complicated. Therefore, it is preferred that the endoscope system should have treatment tools each with power reception efficiency corresponding to the load.

For example, the counter electrode area is set small for a treatment tool for which a power of 1 W is required so that the power reception efficiency of the treatment tool will be $\frac{1}{100}$ of the power reception efficiency of a treatment tool for which a power of 100 W is required. Alternatively, in a treatment tool that requires lower power, the resonant frequency of the power reception unit may be set to deviate from the frequency of the alternating electric field intentionally to reduce the power reception efficiency.

In other words, in an endoscope system including multiple treatment tools, a treatment tool with lower power required for the treatment is so set that the power transmission efficiency between the power transmission unit 19 and the power reception unit 29 will be reduced.

Since an endoscope system including multiple treatment tools, each comprising a power reception unit the power reception efficiency of which is set according to each load, does not need to adjust the output of the power source 30 according to the treatment tool 20, the operability is good.

<Variation 6> Power Conversion

Figure 15:
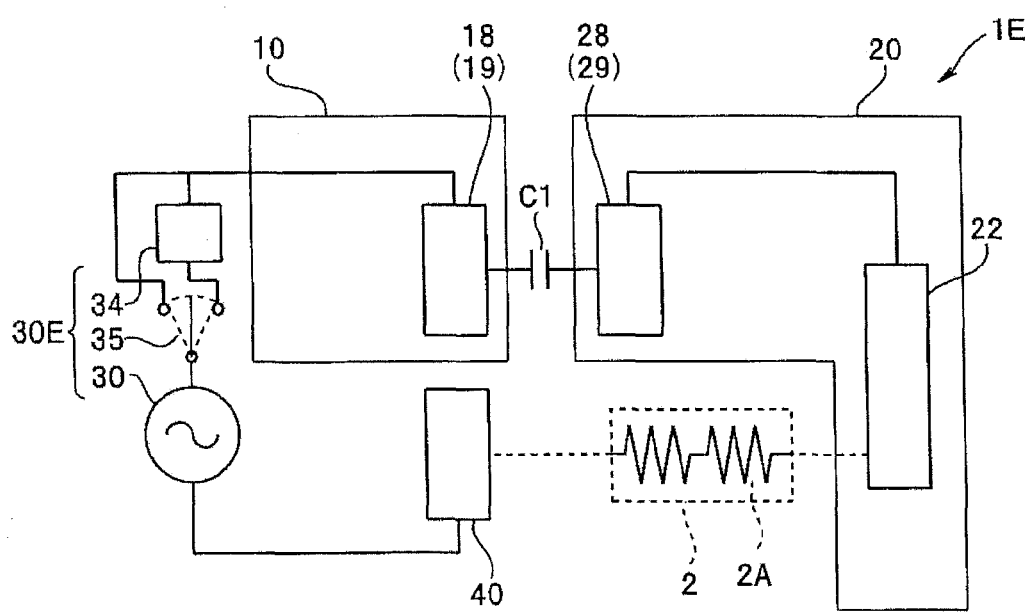
FIG. 15 is an equivalent circuit diagram of an endoscope system as a variation 6 of the first embodiment.

As illustrated in FIG. 15, a power source unit 30E in an endoscope system 1E of a variation 6 has a waveform conversion circuit 34 for converting high-frequency power output from the power source 30 into power with a different waveform. Further, the power source unit 30E has a switch 35 for switching output power to either sinusoidal power output from the power source 30 or power converted by the waveform conversion circuit 34.

The waveform conversion circuit 34 performs amplitude modulation, frequency modulation, or the like on AC waveform high-frequency power having a constant frequency, the amplitude of which does not vary with time and which is output from the power source 30, to output pulse waveform power, attenuation waveform power, square-wave power, or the like.

When the power source 30 is a so-called zero-ohm (0Ω) power supply with low output impedance, the waveform conversion circuit 34 can perform amplitude modulation and frequency modulation. On the other hand, when the power source 30 is a so-called 50Ω power supply with an output impedance of 50Ω, input impedance is lowered in a specific frequency band. Therefore, the waveform conversion circuit 34 can perform only amplitude modulation.

The endoscope system 1E that converts the power output from the power source 30 into power more appropriate to a treatment and outputs the converted power to the treatment unit 22 can do a more appropriate treatment.

<Variation 7>

Figure 16:
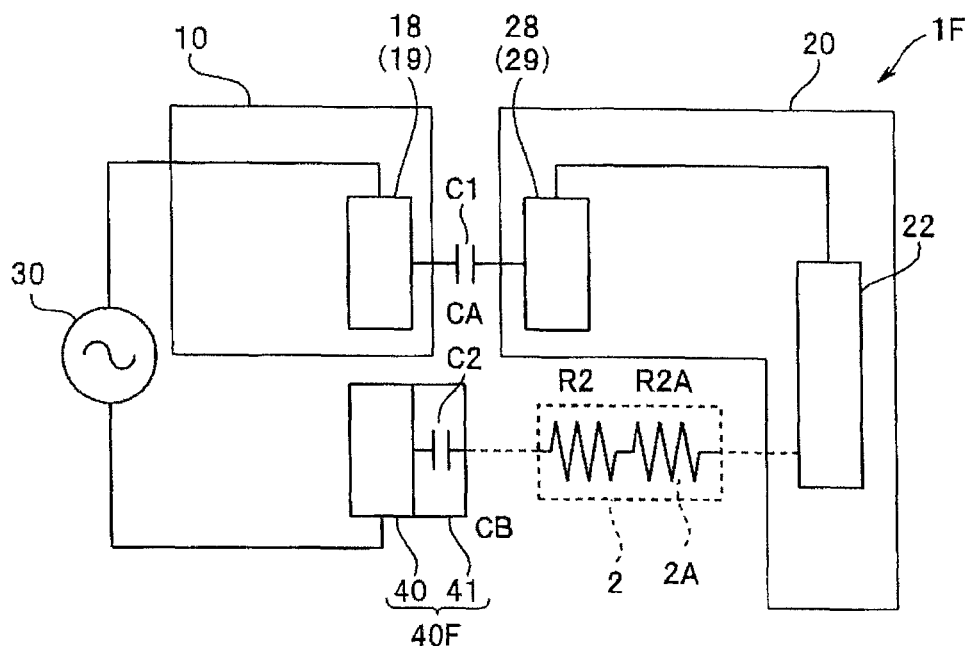
FIG. 16 is an equivalent circuit diagram of an endoscope system as a variation 7 of the first embodiment.
Figure 17:
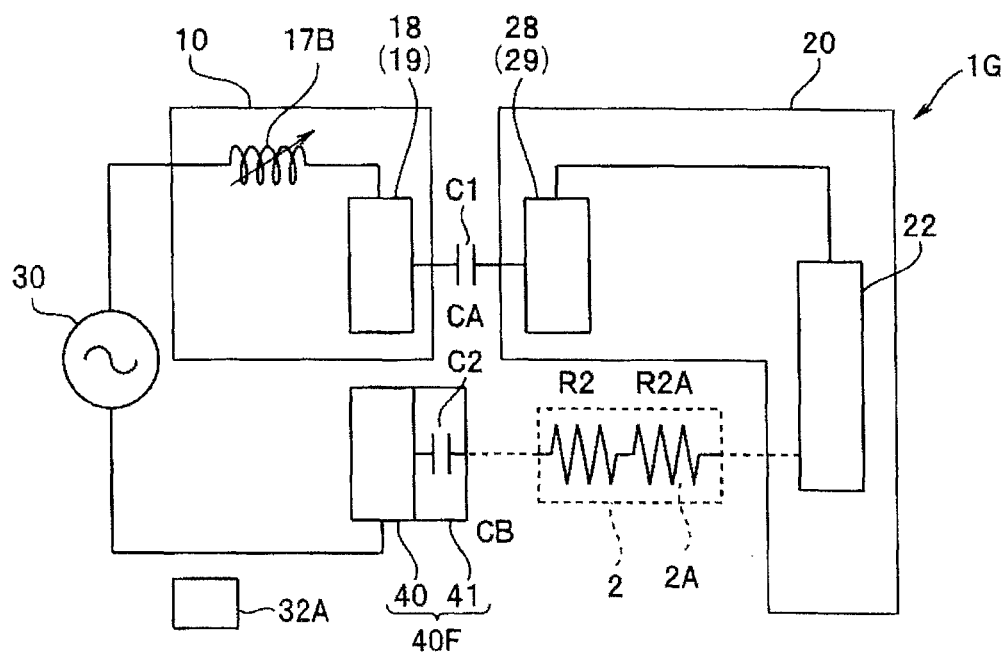
FIG. 17 is an equivalent circuit diagram of an endoscope system as a variation 8 of the first embodiment.

In an endoscope system 1F of a variation 7, as illustrated in FIG. 16, a return electrode 40F is so made that a contact surface of the return electrode 40 as a conductor with a subject 2 to be treated is covered with an insulating material 41.

It is preferred that the insulating material 41 be made of fluorocarbon resin, epoxy resin, polyurethane resin, or the like, and the thickness thereof should be not less than 0.1 mm and not more than 5 mm. The insulation properties can be ensured within the above range or more. When it is within the above range or less, a capacitance CB of a formed capacitor C2 is high, and power transmission efficiency is less likely to be deteriorated.

In other word, as illustrated in an equivalent circuit diagram of FIG. 16, the insulating material 41 functions as the capacitor C2 comprising the capacitance CB in the endoscope system 1F. The capacitor C2 has a large area, and the capacitance CB thereof can also be increased compared with the capacitance CA of the capacitor C1. Therefore, even if the condition of contact between the insulating material 41 and the subject 2 to be treated is unstable, combined capacitance of the capacitor C1 and capacitor C2 does not greatly vary.

The return electrode 40 whose surface is made of metal or the like sometimes makes the subject 2 to be treated uncomfortable when the return electrode 40 is touched. Further, when the condition of contact becomes unstable, the contact resistance increases and this causes current to be likely to concentrate through an unintended path.

On the other hand, the insulating material 41 whose surface is made of resin does not make the subject 2 to be treated uncomfortable compared with the metal. Even when the condition of contact is unstable, since the return circuit becomes stable, where the combined capacitance of the capacitor C1 and the capacitor C2 does not greatly vary, current flowing through an unintended path is less likely to occur.

<Variation 8>

An endoscope system 1G illustrated in FIG. 16 as a combination of the aforementioned embodiment and variations has a combination of the effects of respective endoscope systems.

The endoscope system 1G is an endoscope system including: a flexible endoscope comprising a flexible insertion section including a distal end portion in which an imaging unit is arranged, an operation section arranged on a base end side of the insertion section, and a flexible channel that passes through the insertion section; a treatment tool with a treatment unit that comes into contact with a treated area of an subject to be treated, the treatment unit being inserted from an insertion opening of the operation section, passing through the channel, and protruding from an opening of the distal end portion; a return electrode whose contact surface with the subject to be treated is covered with an insulating material; and a power supply for outputting high-frequency power supplied to the treated area through the treatment unit and the return electrode, wherein the endoscope has a power transmission unit including a transmission electrode laid along a cylindrical outer circumferential surface of the channel to generate an alternating electric field to be applied to the channel by the high-frequency power input from the power source, and the treatment tool has a power reception unit for receiving the alternating electric field generated by the power transmission unit to form, together with the power transmission unit, a resonance circuit comprising a resonant frequency identical to the frequency of the high-frequency power output from the power source, where the power reception unit comprises a reception electrode laid along a cylindrical outer surface and arranged in a position opposite to the transmission electrode in a concentric fashion in a state of inserting the treatment unit into the channel up to a position of protruding from the opening so that the reception electrode will be capacitively coupled to the transmission electrode.

The present invention is not limited to the aforementioned embodiments and the like, and various changes, alterations, combinations, and the like are possible without departing from the spirit of the present invention.

The invention claimed is:

1. An endoscope system comprising:
   an endoscope comprising:
      an endoscope insertion section configured to be inserted into a subject, wherein the endoscope insertion section defines a channel having a distal opening; and
      a power transmission electrode arranged to the endoscope insertion section, wherein the power transmission electrode is electrically connected to a power source configured to output a high-frequency power; and
   a treatment tool comprising:
      an electrically powered treatment device;
      a treatment tool insertion section attached to the electrically powered treatment device, wherein the treatment tool insertion section is configured to be arranged in the channel of the endoscope; and
      a power reception electrode arranged to the treatment tool insertion section,
         wherein the power reception electrode is separated from the power transmission electrode to form a first capacitor to transfer power from the power source through an electric field between the power transmission electrode and the power reception electrode to power the electrically powered treatment device,
   wherein the endoscope further comprises an inductor,
   wherein the inductor and the first capacitor are electrically connected to form a resonant circuit, and
   wherein the resonant circuit has a resonant frequency that coincides with a frequency of the high-frequency power.

2. The endoscope system according to claim 1, wherein the inductor is a variable inductor, and wherein the endoscope further comprises a controller configured to control the variable inductor to adjust the resonant frequency to coincide with the frequency of the high-frequency power.

3. The endoscope system according to claim 1, wherein the power reception electrode comprises a spiral coil.

4. The endoscope system according to claim 1, wherein the treatment tool insertion section is configured in an inserted state to be movably inserted into the channel of the endoscope to protrude the electrically powered treatment device from the distal opening of the channel of the endoscope, and wherein in the inserted state, the power reception electrode is separated from the power transmission electrode to form the first capacitor.

5. The endoscope system according to claim 1, wherein the treatment tool insertion section is configured in an inserted state to be movably inserted into the channel of the endoscope to protrude the electrically powered treatment device from the distal opening of the channel of the endoscope, and wherein in the inserted state, the power reception electrode is concentric with the power transmission electrode.

6. An endoscope system comprising:
an endoscope comprising:
    an endoscope insertion section configured to be inserted into a subject, wherein the endoscope insertion section defines a channel having a distal opening; and
    a power transmission electrode arranged to the endoscope insertion section, wherein the power transmission electrode is electrically connected to a power source configured to output a high-frequency power; and
a treatment tool comprising:
    an electrically powered treatment device;
    a treatment tool insertion section attached to the electrically powered treatment device, wherein the treatment tool insertion section is configured to be arranged in the channel of the endoscope; and
    a power reception electrode arranged to the treatment tool insertion section,
        wherein the power reception electrode is separated from the power transmission electrode to form a first capacitor to transfer power from the power source through an electric field between the power transmission electrode and the power reception electrode to power the electrically powered treatment device,
wherein the electrically powered treatment device comprises a monopolar electrode, and
wherein the endoscope system further comprises a return electrode.

7. The endoscope system according to claim 6, further comprising an insulating material that covers at least a portion of the return electrode,
    wherein in a state in which the monopolar electrode and the insulating material are in contact with the subject, the monopolar electrode, the insulating material and the return electrode form a second capacitor.

8. The endoscope system according to claim 6,
wherein the power reception electrode comprises a spiral coil.

9. The endoscope system according to claim 6,
wherein the treatment tool insertion section is configured in an inserted state to be movably inserted into the channel of the endoscope to protrude the electrically powered treatment device from the distal opening of the channel of the endoscope, and wherein in the inserted state, the power reception electrode is separated from the power transmission electrode to form the first capacitor.

10. The endoscope system according to claim 6,
wherein the treatment tool insertion section is configured in an inserted state to be movably inserted into the channel of the endoscope to protrude the electrically powered treatment device from the distal opening of the channel of the endoscope, and
wherein in the inserted state, the power reception electrode is concentric with the power transmission electrode.

11. An endoscope for use with a treatment tool,
wherein the treatment tool comprises:
    an electrically powered treatment device;
    a treatment tool insertion section attached to the electrically powered treatment device; and
    a power reception electrode arranged to the treatment tool insertion section, and wherein the endoscope comprises:
an endoscope insertion section configured to be inserted into a subject,
    wherein the endoscope insertion section defines a channel having a distal opening, and
    wherein the channel is configured to receive the treatment tool insertion section;
a power transmission electrode arranged to the endoscope insertion section,
    wherein the power transmission electrode is electrically connected to a power source configured to output a high-frequency power, and
    wherein the power transmission electrode is separated from the power reception electrode to form a capacitor to transfer power from the power source through an electric field between the power transmission electrode and the power reception electrode to power the electrically powered treatment device; and
an inductor,
    wherein the inductor and the capacitor form a resonant circuit having a resonant frequency that coincides with a frequency of the high-frequency power.

12. The endoscope according to claim 11,
wherein the inductor is a variable inductor, and
wherein the endoscope further comprises a controller configured to control the variable inductor to adjust the resonant frequency to coincide with the frequency of the high-frequency power.

* * * * *